United States Patent
Kochura et al.

(10) Patent No.: US 11,484,273 B2
(45) Date of Patent: Nov. 1, 2022

(54) DETERMINING FUNCTIONAL AGE INDICES BASED UPON SENSOR DATA

(71) Applicant: International Business Machines Corporation, Armonk, NY (US)

(72) Inventors: Nadiya Kochura, Bolton, MA (US); Fang Lu, Billerica, MA (US)

(73) Assignee: International Business Machines Corporation, Armonk, NY (US)

( * ) Notice: Subject to any disclaimer, the term of this patent is extended or adjusted under 35 U.S.C. 154(b) by 1157 days.

(21) Appl. No.: 15/913,487

(22) Filed: Mar. 6, 2018

(65) Prior Publication Data

US 2019/0274632 A1  Sep. 12, 2019

(51) Int. Cl.
*A61B 5/00* (2006.01)
*A61B 5/16* (2006.01)
(Continued)

(52) U.S. Cl.
CPC .......... *A61B 5/7275* (2013.01); *A61B 5/1118* (2013.01); *A61B 5/165* (2013.01); *G06N 20/00* (2019.01); *G16H 50/30* (2018.01)

(58) Field of Classification Search
CPC ..... A61B 5/7275; A61B 5/1118; A61B 5/165; G16H 50/30; G06N 20/00
See application file for complete search history.

(56) References Cited

U.S. PATENT DOCUMENTS 7,972,779 B2 * 7/2011 Caspi .................. C12Q 1/6883 435/6.12
9,232,066 B2 * 1/2016 Kuang ................ H04M 3/5232
(Continued)

FOREIGN PATENT DOCUMENTS

CN 105640518 A 6/2016
JP 2017000720 A 1/2017

OTHER PUBLICATIONS

Beers, Mark H. Aging as a Risk Factor for Medication-Related Problems. The Consultant Pharmacist, Dec. 1999 (modified Dec. 20, 2004). [9 pages] <http://courses.washington.edu/pharm492/Week2/aging.pdf>.

(Continued)

*Primary Examiner* — Mohamed Barakat
*Assistant Examiner* — Rufus C Point
(74) *Attorney, Agent, or Firm* — The Steadman Law Firm PLLC (57) ABSTRACT

An approach is described with respect to functional age analysis. A method pertaining to such approach may include receiving sensor data collected on a plurality of individuals via a plurality of sensor devices. The method further may include constructing an age indices model by applying machine learning to the collected sensor data. The method further may include determining one or more functional age indices for a subject individual by applying the age indices model to profile data associated with the subject individual. In an embodiment, the method further may include transmitting the one or more functional age indices determined for the subject individual to a professional or a knowledge base, and receiving and processing one or more prescribed recommendations for the subject individual. According to such embodiment, the method further may include updating the age indices model based upon feedback received with respect to the one or more prescribed recommendations.

20 Claims, 6 Drawing Sheets

(51) Int. Cl.
    *A61B 5/11*              (2006.01)
    *G16H 50/30*           (2018.01)
    *G06N 20/00*          (2019.01)

(56) References Cited

U.S. PATENT DOCUMENTS

| | | | | |
|---|---|---|---|---|
| 9,536,269 | B2* | 1/2017 | Chang | G06Q 50/01 |
| 9,721,066 | B1* | 8/2017 | Funaro | G16H 40/63 |
| 2005/0037405 | A1* | 2/2005 | Caspi | A61B 5/7275 |
| | | | | 435/6.11 |
| 2007/0225577 | A1* | 9/2007 | Mathan | G06F 3/011 |
| | | | | 600/301 |
| 2008/0015912 | A1* | 1/2008 | Rosenthal | G06Q 10/063112 |
| | | | | 705/7.14 |
| 2008/0124752 | A1* | 5/2008 | Ryals | G01N 30/7233 |
| | | | | 436/63 |
| 2009/0191521 | A1* | 7/2009 | Paul | A61B 5/165 |
| | | | | 600/300 |
| 2009/0208913 | A1* | 8/2009 | Xu | A61B 5/7264 |
| | | | | 434/169 |
| 2009/0276161 | A1* | 11/2009 | Cobain | A61B 5/7246 |
| | | | | 702/19 |
| 2010/0124756 | A1* | 5/2010 | Ray | G01N 33/6896 |
| | | | | 435/287.9 |
| 2010/0262045 | A1* | 10/2010 | Heaton | G16H 70/00 |
| | | | | 600/595 |
| 2014/0255887 | A1* | 9/2014 | Xu | A61B 5/168 |
| | | | | 434/169 |
| 2015/0017630 | A1* | 1/2015 | Oved | G01N 33/6863 |
| | | | | 435/7.1 |
| 2016/0090097 | A1* | 3/2016 | Grube | G08B 21/06 |
| | | | | 340/576 |
| 2017/0290516 | A1* | 10/2017 | Nguyen | G16H 50/30 |
| 2017/0316174 | A1* | 11/2017 | Wild | G16H 10/20 |
| 2017/0319123 | A1* | 11/2017 | Voss | G16H 30/40 |
| 2018/0107662 | A1* | 4/2018 | Lore | G06F 16/436 |
| 2019/0365332 | A1* | 12/2019 | Fedichev | A61B 5/11 |
| 2020/0397313 | A1* | 12/2020 | Attia | A61B 5/318 |

OTHER PUBLICATIONS

Berke, Ethan M. et al. Objective Measurement of Sociability and Activity: Mobile Sensing in the Community. Annals of Family Medicine, Jul./Aug. 2011, vol. 9, No. 4, pp. 344-350.

IOS Press. Memory complaints and cognitive decline: Data from the GuidAge study. ScienceDaily, Nov. 13, 2017. [4 pages] <https://www.sciencedaily.com/releases/2017/11/171113095443.htm>.

Rosenbloom, Jr., Alfred A. Look beyond a patient's chronological age. Primary Care Optometry News, Oct. 2012. [4 pages] <https://www.healio.com/optometry/low-vision-geriatrics/news/print/primary-care-optometry-news/%7B94d8411e-1cad-4070-b7b5-576f058645e7%7D/look-beyond-a-patients-chronological-age>.

Samuelson, Kristin. Close friends linked to a sharper memory. Medical Xpress, Nov. 1, 2017. [3 pages] <https://medicalxpress.com/news/2017-11-friends-linked-sharper-memory.html>.

* cited by examiner

DETERMINING FUNCTIONAL AGE INDICES BASED UPON SENSOR DATA

BACKGROUND

The various embodiments described herein generally relate to functional age analysis. More specifically, the various embodiments describe techniques of determining one or more functional age indices based upon collected sensor data.

Many life decisions undertaken by or on behalf of individuals conventionally are determined based upon chronological age (i.e., birth age). However, health and general disposition among individuals may vary despite similarities in chronological age. Therefore, measuring age for purposes of determining lifestyle options or recommendations may require consideration of factors beyond chronological age.

SUMMARY

The various embodiments described herein provide techniques of determining one or more functional age indices based upon collection of sensor data. An associated method may include receiving sensor data collected on a plurality of individuals via a plurality of sensor devices embedded in one or more artifacts associated with the plurality of individuals. The method further may include constructing an age indices model by applying machine learning to the collected sensor data. The method further may include determining one or more functional age indices for a subject individual by applying the age indices model to profile data associated with the subject individual. The one or more functional age indices may include a physiological age index, a psychological age index, and a social age index.

In an embodiment, the method further may include transmitting the one or more functional age indices determined for the subject individual to a professional or a knowledge base. According to such embodiment, the method further may include receiving and processing one or more prescribed recommendations for the subject individual. The one or more prescribed recommendations may include one or more treatments or lifestyle modifications. In an additional embodiment, the method further may include receiving feedback with respect to the one or more prescribed recommendations and updating the age indices model based upon the feedback. The feedback may include sensor data collected on the subject individual. Furthermore, collected sensor data may include at least one data type selected from the group consisting of activity data, biosensor data, cognitive data, and emotional data.

According to an embodiment, the step of constructing the age indices model may include defining features of the age indices model, including a plurality of chronological age groups. Additionally, the step of constructing the age indices model may include identifying one or more patterns in the collected sensor data to determine normalized sensor data relevant to each of the plurality of chronological age groups. Additionally, the step of constructing the age indices model may include applying a supervised learning algorithm to the normalized sensor data to train the age indices model. Training the age indices model may include mapping the features of the age indices model to the normalized sensor data. In an embodiment, training the age indices model further may include selecting a group of individuals within one of the plurality of chronological age groups having a specified medical condition and training the age indices model based upon the specified medical condition. In a further embodiment, the supervised learning algorithm may be a multiclass classification algorithm. Moreover, the step of constructing the age indices model may include, responsive to training the age indices model, defining a plurality of functional age indices.

According to a further embodiment, the step of identifying the one or more patterns in the collected sensor data may include constructing an average values vector based upon the collected sensor data and clustering the collected sensor data via data mining. The step of clustering the collected sensor data may include identifying cluster outliers by calculating respective distances from the average values vector and comparing the respective distances against one or more predetermined thresholds. The step of clustering the collected sensor data further may include creating a plurality of clusters of normalized sensor data relevant to each of the plurality of chronological age groups. The clusters of normalized sensor data may exclude the cluster outliers. In addition, the step of identifying the one or more patterns in the collected sensor data may include creating at least one correlation between the cluster outliers and a set of activities respectively associated with the cluster outliers and creating at least one correlation between the clusters of normalized sensor data and a set of activities respectively associated with the clusters of normalized sensor data. In a further embodiment, the step of constructing the average values vector may include determining a features vector based upon the clustered sensor data, wherein each feature of the features vector may represent a particular sensor measurement in a particular context, and determining the average values vector based upon the features vector.

An additional embodiment includes a computer program product including a computer readable storage medium having program instructions embodied therewith. According to such embodiment, the program instructions may be executable by a computing device to cause the computing device to perform one or more steps of above recited method. A further embodiment includes a system having a processor and a memory storing an application program, which, when executed on the processor, performs one or more steps of the above recited method.

BRIEF DESCRIPTION OF THE DRAWINGS

So that the manner in which the above recited aspects are attained and can be understood in detail, a more particular description of embodiments, briefly summarized above, may be had by reference to the appended drawings.

Note, however, that the appended drawings illustrate only typical embodiments of this invention and are therefore not to be considered limiting of its scope, for the invention may admit to other equally effective embodiments.

DETAILED DESCRIPTION

The various embodiments described herein are directed to techniques of determining one or more functional age indices. The one or more functional age indices may be determined based upon collection of sensor data and construction of an age indices model by applying machine learning to the collected sensor data. The one or more functional age indices may include a physiological age index, a psychological age index, and/or a social age index.

The various embodiments described herein may have advantages over conventional techniques. Specifically, by determining one or more functional age indices based upon an age indices model, the various embodiments may enable one or more prescribed recommendations for a subject individual that may be more appropriate for such individual than recommendations provided solely or primarily based upon chronological age. Additionally, the various embodiments may enable improvement of model accuracy and scope based upon collection and application of feedback (implicit or explicit) with respect to one or more prescribed recommendations. Furthermore, the various embodiments may enable training an age indices model based upon one or more specified medical conditions, such that the one or more specified medical conditions may influence the one or more functional age indices determined for an individual and accordingly may duly influence any prescribed recommendations for such individual. Therefore, training an age indices model according to the various embodiments may enable dynamic adjustment of prescribed recommendations over time as data is collected and processed. Moreover, according to the various embodiments, one or more functional age indices determined for an individual may be adjusted over time based upon collection of new sensor data and/or based upon collection and application of feedback. Some of the various embodiments may not include all such advantages, and such advantages are not necessarily required of all embodiments.

In the following, reference is made to various embodiments of the invention. However, it should be understood that the invention is not limited to specific described embodiments. Instead, any combination of the following features and elements, whether related to different embodiments or not, is contemplated to implement and practice the invention. Furthermore, although embodiments may achieve advantages over other possible solutions and/or over the prior art, whether or not a particular advantage is achieved by a given embodiment is not limiting. Thus, the following aspects, features, embodiments, and advantages are merely illustrative and are not considered elements or limitations of the appended claims except where explicitly recited in a claim(s) Likewise, reference to "the invention" shall not be construed as a generalization of any inventive subject matter disclosed herein and shall not be considered to be an element or limitation of the appended claims except where explicitly recited in a claim(s).

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network, and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++, or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions also may be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions also may be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The various embodiments described herein may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in the cloud, without regard for the underlying physical systems (or locations of those systems) used to provide the computing resources.

Typically, cloud computing resources are provided to a user on a pay-per-use basis, where users are charged only for the computing resources actually used (e.g., an amount of storage space consumed by a user or a number of virtualized systems instantiated by the user). A user can access any of the resources that reside in the cloud at any time, and from anywhere across the Internet. In context of this disclosure, workloads of a client computing system or server system running an application according to the various embodiments described herein may be deployed to a computing cloud. Moreover, cloud-based database systems, virtual machines, and a variety of other server applications may be used to manage such workloads.

Particular embodiments herein describe techniques of determining one or more functional age indices. However, it should be understood that the techniques described herein may be adapted to a variety of purposes in addition to those specifically described herein. Accordingly, references to specific embodiments are included to be illustrative and not limiting.

Figure 1:
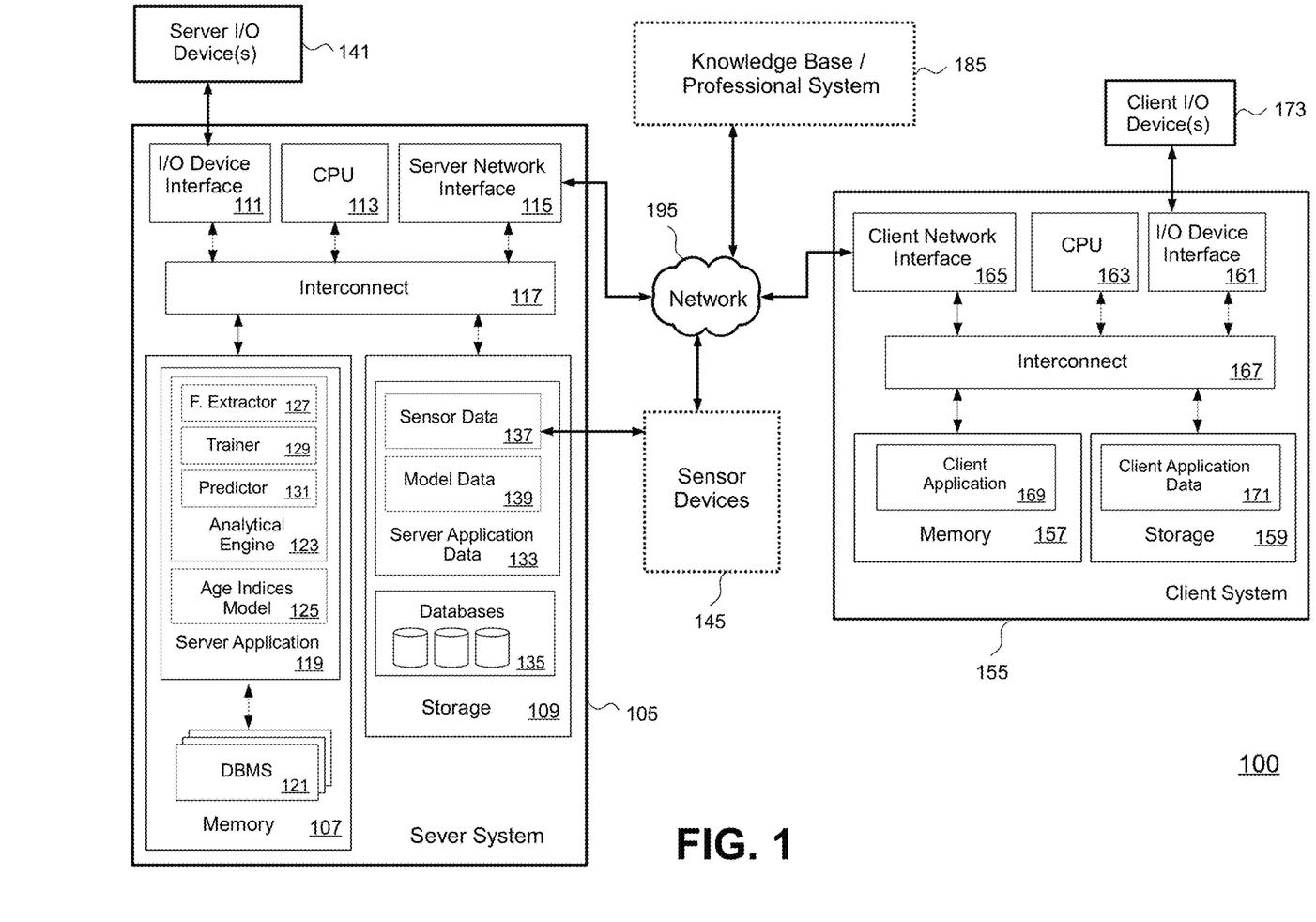
FIG. 1 illustrates a computing infrastructure, according to an embodiment.

FIG. 1 illustrates a computing infrastructure 100, according to an embodiment. As shown, computing infrastructure 100 includes server system 105, sensor devices 145, client computing system 155, and a knowledge base and/or professional computing system 185, each of which may be connected to a communications network 195. Although server system 105 and client computing system 155 are illustrated in FIG. 1, computing infrastructure 100 may include any number of computing systems and more specifically may include any number of server systems and/or client systems. Computing infrastructure 100 may include any number of sensor devices 145. Sensor devices 145 may be embedded in one or more artifacts associated with a plurality of individuals. Each of the sensor devices 145 may include one or more physical computing components, including a CPU, memory, storage, and/or a network interface. Server system 105, client computing system 155, and/or other computing systems may communicate with knowledge base and/or professional computing system 185 in order to determine one or more prescribed recommendations for a subject individual in accordance with the various embodiments described herein. A professional computing system in such context may be a computing device associated with a professional (e.g., a medical specialist).

Illustratively, server system 105 may include a memory 107, storage 109, a server I/O device interface 111, a CPU 113, and a server network interface 115, all of which may be interconnected via interconnect 117 (e.g., a bus). Although shown as a single computing system, server system 105 is included to be representative of a single server system or multiple server systems. Although server system 105 is illustrated in FIG. 1, computing infrastructure 100 may include any number of server systems. Memory 107 may include a server application 119 and a database management system (DBMS) 121. Server application 119 may determine one or more functional age indices according to one or more of the various embodiments described herein. DBMS 121 is included to be representative of a single database management system or multiple database management systems. According to a further embodiment, server application 119 may interact with separate database management systems. Server application 119 may include analytical engine 123 and age indices model 125. Analytical engine 123 may include a plurality of components, including but not limited to a feature extractor component 127, a trainer component 129, and a predictor component 131.

Storage 109 may include server application data 133 and databases 135. Server application 119 may generate and process server application data 133 based upon interaction with client computing system 155, sensor devices 145, and/or one or more other systems via network 195. Server application 119 may send to DBMS 121 a database query request, and DBMS 121 may process such query. DBMS 121 may include a software application configured to manage databases 135. Databases 135 may include one or more ontology trees or other ontological structures. While FIG. 1 illustrates three databases 135, computing infrastructure 100 may include any number of databases. According to an embodiment, DBMS 121 may send one or more requests to remote databases (not shown) via network 195. Server application data 133 may include sensor data 137 and model data 139. Server system 105 may receive sensor data 137 from one or more sensor devices 145. Analytical engine 123 of server application 119 may process unstructured sensor data 137 in order to generate model data 139. Furthermore, analytical engine 123 may extract features from sensor data 137, e.g., via feature extractor component 127, in order to generate features of age indices model 125.

Server I/O device interface 111 may be communicatively coupled to one or more server I/O devices 141. CPU 113 is included in FIG. 1 to be representative of a single CPU, multiple CPUs, a single CPU having multiple processing cores, or the like. Server network interface 115 may receive data from, and/or may transmit data to, client computing system 155, knowledge base and/or professional computing system 185, or another system via network 195. For instance, server application 119 may process a request pertaining to age indices model 125 sent by client computing system 155 to server system 105 via server network interface 115. Additionally or alternatively, server application 119 may transmit one or more functional age indices determined for a subject individual to knowledge base and/or professional computing system 185 via server network interface 115. Additionally or alternatively, server application 119 may transmit data to client computing system 155 via server network interface 115. Additionally or alternatively, server application 119 may receive one or more prescribed recommendations for a subject individual from knowledge base and/or professional computing system 185 via server network interface 115.

Client computing system 155 may include a memory 157, storage 159, a client I/O device interface 161, a central processing unit (CPU) 163, and a client network interface 165, all of which may be interconnected via interconnect 167 (e.g., a bus). Although shown as a single computing system, client computing system 155 is included to be representative of a single client or multiple clients within computing infrastructure 100. In an embodiment, client computing system 155 may function as a thin client. Client computing system 155 according to the various embodiments described herein may be a mobile device (e.g., a smart phone, a feature phone, a tablet device, a laptop, etc.). Alternatively, client computing system 155 may be a stationary device (e.g., a desktop computer).

Memory 157 may include a client application 169. Client application 169 may be an online or network application configured for interfacing with server system 105 and/or other computing systems. Storage 159 may include client application data 171 associated with client application 169. Client I/O device interface 161 may be communicatively coupled to one or more client I/O devices 173. CPU 163 is included in FIG. 1 to be representative of a single CPU, multiple CPUs, a single CPU having multiple processing cores, or the like. Client network interface 165 may receive data from, and may transmit data to, server system 105 via network 195. Furthermore, client computing system 155 may be configured to interface with other client systems and/or server systems in computing infrastructure 100.

According to an embodiment, client application 169 of client computing system 155 may send to server system 105 a functional age request with respect to a subject individual. The functional age request may include the chronological age of the subject individual. Additionally, the functional age request may include profile data associated with the subject individual or a reference to such profile data. The functional age request may pertain to physiological age, psychological age, and/or social age. Additionally or alternatively, the functional age request may pertain to another age-related aspect. The subject individual or a user associated with the subject individual may send the functional age request to the server system 105 via an interface associated with client application 169 (e.g., client network interface 165), and in turn server application 119 of server system 105 may receive the functional age request via server network interface 115. Alternatively, knowledge base and/or professional computing system 185 may send the functional age request to the server system 105, and in turn server application 119 may receive the functional age request via server network interface 115.

Figure 2A:
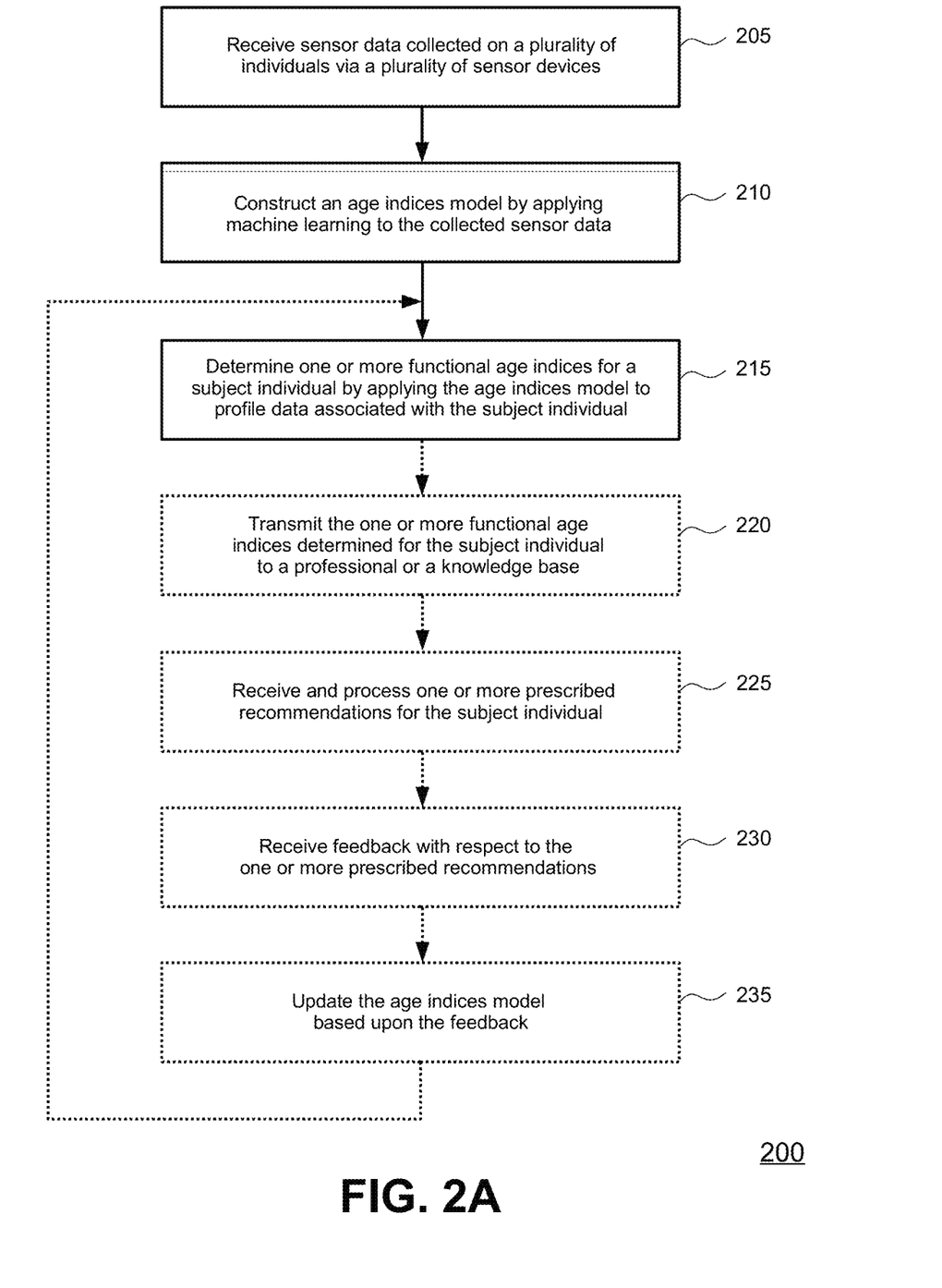
FIG. 2A illustrates a method of determining one or more functional age indices based upon collection of sensor data, according to an embodiment.

FIG. 2A illustrates a method 200 of determining one or more functional age indices. One or more steps associated with the method 200 and the other methods described herein may be carried out in a client-server computing environment (e.g., computing infrastructure 100). Additionally or alternatively, one or more steps associated with the method 200 and the other methods described herein may be carried out within one or more workloads of a cloud computing environment. Additionally or alternatively, one or more steps associated with the method 200 and the other methods described herein may be carried out in a peer-to-peer network environment, in which case the method steps described herein may be carried out via a peer application of a peer computing system.

A server application of a server system (e.g., sever application 119 of server system 105) may facilitate processing according to the method 200. The server application may include, or otherwise may be associated with, an analytical engine (e.g., analytical engine 123). The method 200 may begin at step 205, where the server application may receive sensor data collected on a plurality of individuals (e.g., sensor data 137). The sensor data may be collected via a plurality of sensor devices (e.g., sensor devices 145). The plurality of sensor devices may be embedded in one or more artifacts associated with the plurality of individuals. Specifically, the plurality of sensor devices may be embedded in clothes, shoes, utensils, eyeglasses, or other objects respectively associated with the plurality of individuals. Furthermore, in an embodiment, the plurality of sensor devices may be embedded on or within the respective bodies of the plurality of individuals (e.g., on skin or underneath skin). For instance, one or more sensor devices among the plurality of sensor devices may include wearable sensors that measure physiological biomarkers, such as electrocardiography (electrical activity of the heart), skin temperature, respiratory rate, electromyography (muscle activity), and/or gait (posture).

In an embodiment, one or more sensor devices among the plurality of sensor devices further may include sensors, e.g., waist-mounted or arm-mounted sensors, which continuously capture data pertaining to behavior and environment. Such sensors may include an accelerometer, a microphone, a barometer, and/or sensors for temperature, humidity, and light. In a further embodiment, one or more sensors among the plurality of sensor devices may include motion sensors (e.g., accelerometers, gyroscopes, position or location sensors, pressure sensors, etc.) that measure time spent by an individual walking level, walking up/down an elevation, or standing/sitting in a stationary position. Such sensors additionally may determine geographic position of an individual at a given point in time. In a further embodiment, one or more sensors among the plurality of sensor devices may include microphone-based sensors for measuring time spent by an individual conversing with or otherwise interacting with other individuals. In a further embodiment, one or more sensors among the plurality of sensor devices may collect data pertaining to social media activities and/or activities recorded in a calendar/personal scheduler. In a further embodiment, one or more sensors among the plurality of sensor devices may collect data pertaining to cognitive services and applications, such as speech-to-text, image recognition, and/or sentiment/tone analytics.

The sensor data collected on the plurality of individuals via the plurality of sensor devices and received by the server application at step 205 may assume multiple forms, including text data (e.g., calendar entries or written/typed records authored by or otherwise associated with one or more individuals among the plurality of individuals), audiovisual data (e.g., voice samples or sound recordings), and/or images (e.g., photographs or drawings). Generally, the sensor data may include information with respect to one or more individuals, including information pertaining to social interactions, daily activities, reactions, and/or body measurements. Additionally, the sensor data may include at least one data type selected from the group consisting of activity data, biosensor data, cognitive data, and emotional data. Such data types are not exhaustive; the sensor devices also may collect other data types.

Activity data collected on one or more individuals among the plurality of individuals may include, but is not limited to, type, duration, and/or frequency of social or cultural activities undertaken by the individual and the level of interest therein. Activity data collected on the one or more individuals further may include individual preferences, such as type and/or quantity of food consumed or audiovisual media tastes. Activity data collected on the one or more individuals further may include type, duration, and/or frequency of interactions with other individuals (including contents of communications with other individuals and/or identities of other individuals) as well as the respective ages or age range of other individuals with whom the one or more individuals interact. Such activity data further may include information regarding interactions between the one or more individuals and animals (e.g., a pet). Activity data collected on the one or more individuals further may indicate the frequency at which the one or more individuals read, write, and converse with respect to certain types of topics. Activity data collected on the one or more individuals further may indicate the type, duration, and/or frequency of physical fitness activities completed (cardiovascular, exercise, lifting weights, reducing inactivity, etc.).

Biosensor data collected on one or more individuals among the plurality of individuals may include, but is not limited to, biometric data pertaining to measurable attributes. Such biometric data may include blood pressure, respiratory capacity, aerobic power, blood glucose level, and physical attributes classified into biological state categories, such as perspiration level, heartbeat, and body temperature. The sensor devices may detect such biometric data via biometric sensors placed on, within, or in close proximity to the respective bodies of the one or more individuals.

Cognitive data collected on one or more individuals among the plurality of individuals may include, but is not limited to, data pertaining to cognitive functioning. Such cognitive data may include data pertaining to stress/anxiety levels. The sensor devices may detect stress/anxiety levels via sensors detecting voice patterns, facial expressions, and/or gestures of the one or more individuals. The cognitive data further may include data pertaining to memory. The sensor devices may detect memory issues via sensors analyzing phrases spoken by the one or more individuals and/or interaction with other individuals.

Emotional data collected on one or more individuals among the plurality of individuals may include, but is not limited to, data pertaining to emotional state. Such emotional data may include polarity of emotion (positive, negative, neutral) and/or intensity of emotion. The sensor devices may detect such emotional data via sensors detecting voice patterns, vocal pitch/tone, facial expressions, and/or gestures of the one or more individuals.

At step 210, the server application may construct an age indices model (e.g., age indices model 125) by applying machine learning to the collected sensor data. An embodiment with regard to constructing the age indices model according to step 210 is described with respect to FIG. 3. The analytical engine associated with the server application may facilitate organization and evaluation of the collected sensor data received at step 205 for purposes of constructing the age indices model at step 210. In an embodiment, as the collected sensor data received at step 205 may be unstructured, a feature extractor component of the analytical engine (e.g., feature extractor component 127) may facilitate evaluation of the unstructured sensor data in order to extract features for use within the age indices model. According to an embodiment, the server application may construct the age indices model by utilizing multiple forms of artificial intelligence, including both semi-supervised machine learning for purposes of clustering collected sensor data and supervised machine learning for purposes of training the age indices model. Embodiments with respect to clustering the collected sensor data and training the age indices model are described further herein with respect to FIGS. 3-5. In a further embodiment, the server application may utilize unsupervised machine learning in the context of sensor data exploration, though constructing the age indices model generally may require labeled data points.

At step 215, the server application may determine one or more functional age indices for a subject individual by applying the age indices model to profile data associated with the subject individual. Specifically, the server application may identify and analyze profile data associated with the subject individual. Profile data associated with the subject individual may include, but is not limited to, social networking data, any textual documents authored by or otherwise related to the subject individual, and/or any audiovisual media authored by or otherwise related to the subject individual. Additionally, profile data associated with the subject individual may include input provided by the subject individual responsive to one or more inquiries (e.g., health surveys, activity questionnaires, etc.). The server application may identify any other form of data associated with the subject individual as profile data in the context of step 215.

In an embodiment, the one or more functional age indices determined at step 215 may include a physiological age index, a psychological age index, and/or a social age index. A physiological age index may reflect one or more age factors pertaining to physical health. In determining a physiological age index, the server application may focus upon biometric data, exercise data, data from a specified range of physical medical tests or examinations (e.g., based upon tests of either a wide range of body systems or a more specialized range focusing on relatively fewer body systems), etc. A psychological age index may reflect one or more age factors pertaining to mental or cognitive health. In determining a psychological age index, the server application may focus upon data from a specified range of mental/cognitive medical tests or examinations and/or other data pertaining to anxiety/stress level, memory, learning ability, self-esteem, data, self-efficacy, perception, etc. A social age index may reflect one or more age factors pertaining to expectations of behavior or interpersonal/cultural interaction. In determining a social age index, the server application may focus upon data pertaining to behavioral expectation and/or level of social isolation as applied to individuals of varying age (e.g., expectations regarding activities performed, driving habits, and the like) as well as data pertaining to social interaction, cultural norms, etc.

In an embodiment, the server application may determine the one or more functional age indices for the subject individual in response to a functional age indices request. The server application may receive a functional age indices request from a user of a client application (e.g., client application 169 of client computing system 155). The user of the client application may be the subject individual or someone associated with the subject individual. In a further embodiment, determination of one or more functional age indices according to step 215 may be facilitated via a predictor component of the analytical engine (e.g., predictor component 131). According to a further embodiment, a functional age index determined according to step 215 may be an integer value (e.g., the server application may determine a physiological age index of sixty for the subject individual). According to an additional or alternative embodiment, a functional age index determined according to step 215 may be a specified range (e.g., the server application may determine a physiological age index range of sixty to sixty-five for the subject individual). For instance, while the subject individual may have a chronological age of fifty, the server application may determine at step 215 that the subject individual has a physiological age index range of sixty to sixty-five due to physical inactivity and/or a health condition. Accordingly, by providing one or more functional age indices, the age indices model may quantify divergence of functional age from chronological age based upon one or more effects of the aging process upon the subject individual, especially later in life when various maladies and/or disabilities may emerge. The divergence of functional age from chronological age may be negative, which in the above instance results in a physiological age index range for the subject individual that exceeds the chronological age of the subject individual. Conversely, the divergence of functional age from chronological age may be positive. For instance, the social age index or social age index range for the subject individual may be less than his or her chronological age if the subject individual is outgoing relative to peers and participates in numerous cultural activities.

Optionally, at step 220 the server application may transmit the one or more functional age indices determined for the subject individual to a professional and/or a knowledge base (e.g., knowledge base and/or professional computing system 185). In an embodiment, in the event that a functional age indices request is sent by a professional associated with the subject individual, at step 220 the server application may transmit the one or more functional age indices determined at step 215 to such professional. In an alternative embodiment, in the event that a functional age indices request is sent by the subject individual via the client application, at step 220 the server application may transmit the one or more functional age indices determined at step 215 to any professional designated by the subject individual (e.g., a doctor) and/or to a knowledge base (e.g., a database or ontology) for further analysis. According to such alternative embodiment, the server application also may transmit the one or more functional age indices determined at step 215 to the subject individual via the client application.

Optionally, at step 225 the server application may receive and process one or more prescribed recommendations for the subject individual in response to the transmission at step 220. The one or more prescribed recommendations for the subject individual may include one or more treatments or lifestyle modifications. More specifically, the one or more prescribed recommendations may include medication dosage, one or more activity adjustments, one or more diet recommendations, and/or a treatment plan. The server application may receive the one or more prescribed recommendations directly from the professional and/or from the knowledge base to which the server application transmitted the one or more functional age indices at step 220. Alternatively, the server application may receive the one or more prescribed recommendations from an administrator associated with the professional and/or from an administrative agent associated with the knowledge base. The server application may process the one or more prescribed recommendations by presenting them to the subject individual upon receipt. Specifically, in the event that a functional age indices request is sent by the subject individual via the client application, the server application may transmit to the subject individual the one or more prescribed recommendations upon receipt in addition to, or in lieu of, the one or more functional age indices. Additionally or alternatively, the server application may provide the one or more prescribed recommendations to the subject individual via an alternative technique. For instance, the server application may post the one or more prescribed recommendations on an online interface available to the subject individual. Additionally or alternatively, the professional (or an administrator associated with the professional) and/or the knowledge base (or an administrative agent associated with the knowledge base) may transmit the one or more prescribed recommendations directly to the subject individual.

Optionally, at step 230 the server application may receive feedback with respect to the one or more prescribed recommendations. The feedback may include implicit feedback, e.g., in the form of sensor data collected on the subject individual. Such implicit feedback may indicate whether the subject individual is complying with or has complied with the one or more prescribed recommendations. Additionally or alternatively, the feedback may include explicit feedback, e.g., in the form of input from the subject individual or another individual associated with the subject individual, such as the professional who issued the one or more prescribed recommendations or another professional. Such explicit feedback may be provided to the server application via a conversational agent learning model (e.g., a computer application that facilitates audiovisual conversation or other interaction, such as a chatbot) or via another interactive interface. Optionally, at step 235 the server application may update the age indices model based upon the feedback. According to an embodiment, the server application may determine whether the feedback is positive, negative, or neutral. In the event that the feedback is positive, the server application may update the age indices model to create one or more positive correlations between the one or more prescribed recommendations and model aspects pertaining to determining the one or more functional age indices. Conversely, in the event that the feedback is negative, the server application may update the age indices model to create one or more negative correlations between the one or more prescribed recommendations and model aspects pertaining to determining the one or more functional age indices. Based upon an updated application of the age indices model, the server application may determine any change (favorable or unfavorable) to the one or more functional age indices of the subject based upon the one or more prescribed recommendations. Accordingly, the method 200 optionally may return to step 215 upon update of the age indices model based upon the feedback at step 235 so that that server application may determine any update(s) to the one or more functional age indices.

Figure 2B:
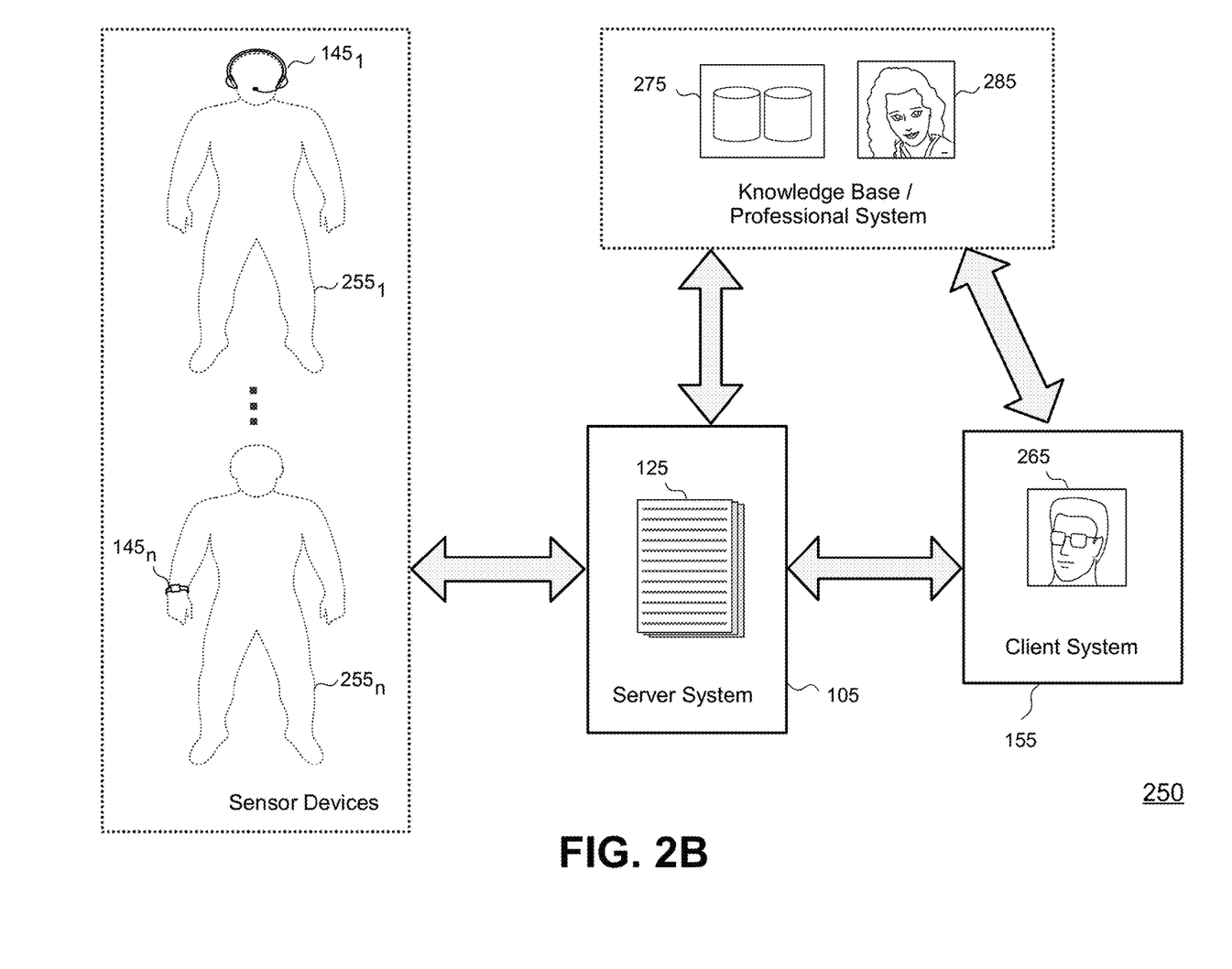
FIG. 2B illustrates a schematic diagram with respect to determining one or more functional age indices based upon collection of sensor data, according to an embodiment.

FIG. 2B illustrates a schematic diagram 250 with respect to determining one or more functional age indices according to the method 200 in the context of computing infrastructure 100. Diagram 250 is merely an example illustration and is not intended to limit potential applications of steps of the method 200 or other steps associated with the various embodiments. Server application 119 of computing infrastructure 100 may construct age indices model 125 according to step 210 based upon sensor data received at server system 105 according to step 205 and collected from sensor devices $145_1$ to $145_n$ embedded in respective artifacts associated with a plurality of individuals $255_1$ to $255_n$. More specifically, as shown in FIG. 2B, sensor device $145_1$ may include a microphone-based sensor for detecting voice patterns of individual $255_1$, and sensor device sensor device $145_n$ may include a wristwatch-based sensor for detecting pulse or other biometrics associated with individual $255_n$.

Furthermore, according to step 215, server application 119 of server system 105 may interface with client application 169 of client computing system 155 to determine one or more functional age indices for subject individual 265. Additionally, according to step 220, server application 119 may transmit the one or more functional age indices for subject individual 265 to a knowledge base 275 and/or a professional 285. According to step 225, server application 119 may receive and process one or more prescribed recommendations for subject individual 265. Server application 119 may receive the one or more prescribed recommendations from knowledge base 275 and/or professional 285. Additionally or alternatively, subject individual 265 at client computing system 155 may receive the one or more prescribed recommendations. Furthermore, according to step 230, server application 119 of server system 105 may receive feedback with respect to the one or more prescribed recommendations, e.g., in the form of implicit feedback from collected sensor data associated with subject individual 265 and/or explicit feedback from subject individual 265, knowledge base 275, and/or professional 285. According to step 235, server application 119 may update age indices model 125 based upon the received feedback.

Figure 3:
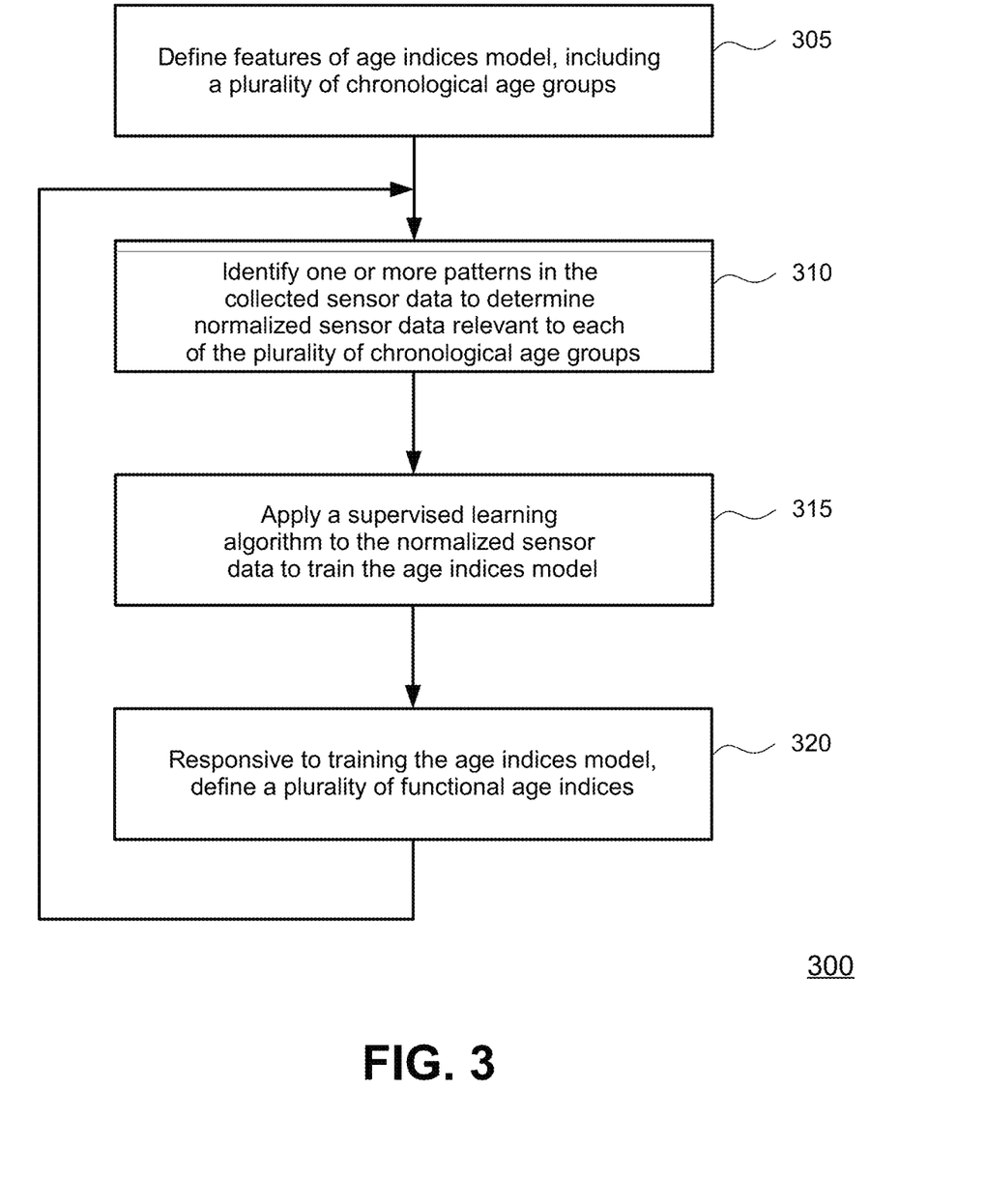
FIG. 3 illustrates a method of constructing an age indices model, according to an embodiment.

FIG. 3 illustrates a method 300 of constructing the age indices model, according to an embodiment. The method 300 provides an example embodiment with respect to step 210 of the method 200. The method 300 may begin at step 305, where the server application described in the context of the method 200 may define features of the age indices model. The features of the age indices model may include a plurality of chronological age groups. In an embodiment, the chronological age groups may correspond to defined age ranges of equal size, e.g., of ten years [{0-9, 10-19, 20-29, . . . }], of five years [{0-4, 5-9, 10-14, . . . }], etc. Alternatively, the chronological age groups may correspond to defined age ranges of varying size, e.g., {0-5, 6-18, 19-34, 35-49, 50-64, 65+}. According to an embodiment, the feature extractor component of the analytical engine may facilitate definition of the plurality of chronological age groups and other features of the age indices model by analyzing the sensor data received from the sensor devices and extracting features from the sensor data for classification in the context of the model.

At step 310, the server application may identify one or more patterns in the collected sensor data to determine normalized sensor data relevant to each of the plurality of chronological age groups. An embodiment with regard to identifying one or more patterns in the collected sensor data according to step 310 is described with respect to FIG. 4. At step 315, the server application may apply a supervised learning algorithm to the normalized sensor data to train the age indices model. In an embodiment, the supervised learning algorithm applied at step 315 may be a multiclass classification algorithm. Such multiclass classification algorithm may be a multinomial logistic regression algorithm. Alternatively, such multiclass classification algorithm may be a neural network algorithm. Alternatively, such multiclass classification algorithm may be a decision tree algorithm. Training the age indices model may comprise mapping the features of the age indices model to the normalized sensor data. In an embodiment, a trainer component of the analytical engine (e.g., trainer component 129) may facilitate mapping the features of the age indices model to the normalized sensor data. By training the age indices model, the server application may continuously and/or repeatedly map sensor data to model features over time as the new sensor data is received and normalized. The frequency at which the server application trains the age indices model may be periodic and/or may be determined by an administrator associated with the server system.

In an embodiment, training the age indices model further may comprise selecting a group of individuals within one of the plurality of chronological age groups having a specified medical condition and training the age indices model based upon the specified medical condition. In accordance with such embodiment, the server application may apply distinct features of the age indices model based upon the specified medical condition. Therefore, the one or more functional age indices determined for the subject individual by the server application at step 215 may be context based such that any specified medical condition may be reflected. Accordingly, the age indices model may incorporate distinctions among various groups beyond chronological age. Moreover, the one or more prescribed recommendations received at step 225 may reflect any specified medical condition. For instance, in the context of determining one or more functional age indices for the subject individual, the server application (and more specifically, the analytical engine) may identify any medical condition associated with the subject individual and may apply the age indices model by comparing data of the subject individual (e.g., biometric data or cognitive data) with analogous data of other individuals having the medical condition. Accordingly, the server application may determine the one or more functional age indices for the subject individual based upon the training of the model at step 315 in the context of the medical condition, and furthermore one or more prescribed recommendations for the subject individual may reflect the medical condition.

At step 320, responsive to training the age indices model, the server application may define a plurality of functional age indices. By training the age indices model though application of the supervised learning algorithm at step 315, at step 320 the server application may associate the normalized sensor data with one or more of the plurality of chronological age groups, and such associations may provide a basis for associations between the normalized sensor data and one or more functional age indices. Accordingly, the server application may store or otherwise record in the age indices model correlations between normalized sensor data relevant to each of the plurality of chronological age groups and the one or more functional age indices. The correlations may include activities, behaviors, etc. attributed to various functional age index values and/or functional age index ranges. For instance, based upon training the age indices model at step 315, at step 320 the server application may determine that certain types of activities generally correlate with individuals having a physiological age index of forty. Accordingly, the server application may store/record a correlation between the certain types of activities and a physiological age index of forty. As an additional example, based upon training the age indices model at step 315, at step 320 the server application may determine that a certain score on a cognitive test generally correlates with individuals having a psychological age index of sixty. Accordingly, the server application may store/record a correlation between the certain score on the cognitive test and a psychological age index of sixty. As an additional example, based upon training the age indices model at step 315, at step 320 the server application may determine that a certain social behavior generally correlates with individuals having a social age index range of eighty to ninety. Accordingly, the server application may store/record a correlation between the certain social behavior and a social age index range of eighty to ninety. Since training the age indices model may include mapping continuously and/or repeatedly received and normalized sensor data to the features of the age indices model, the method 300 may return to step 310 upon definition of the plurality of functional age indices so that the plurality of functional age indices may be refined as the server application receives and normalizes new sensor data.

In an embodiment, in the context of constructing the age indices model according to the method 300, for each of the functional age indices defined in accordance with step 320, the server application may define features, may determine normalized sensor data, and may train a separate age index model. According to such embodiment, the server application may determine normalized physiological sensor data and may train a physiological index model based upon features defined from metrics collected from biosensors, motion sensors, wearable sensors, etc. Based upon patterns in the collected sensor data identified according to step 310, the server application may label physiological data with various levels of granularity, e.g., data may be labeled based upon correlation with respect to certain biometric thresholds or certain levels of physical activity. Furthermore, according to such embodiment, the server application may determine normalized psychological sensor data and may train a psychological index model based upon features defined from metrics that measure emotional state and/or cognitive state. Based upon patterns in the collected sensor data identified according to step 310, the server application may label psychological data with various levels of granularity, e.g., data may be labeled based upon correlation with respect to a certain level of depression or with respect to a certain predefined personality type. Additionally, according to such embodiment, the server application may determine normalized social sensor data and may train a social index model based upon features defined from metrics that measure behavioral tendencies and/or communicative tendencies. Based upon patterns in the collected sensor data identified according to step 310, the server application may label social data with various levels of granularity, e.g., data may be labeled based upon correlation with respect to certain defined behavioral standards and/or communicative standards. According to such embodiment, the physiological index model, psychological index model, and social index model may be separate constituent components of the age indices model.

Figure 4:
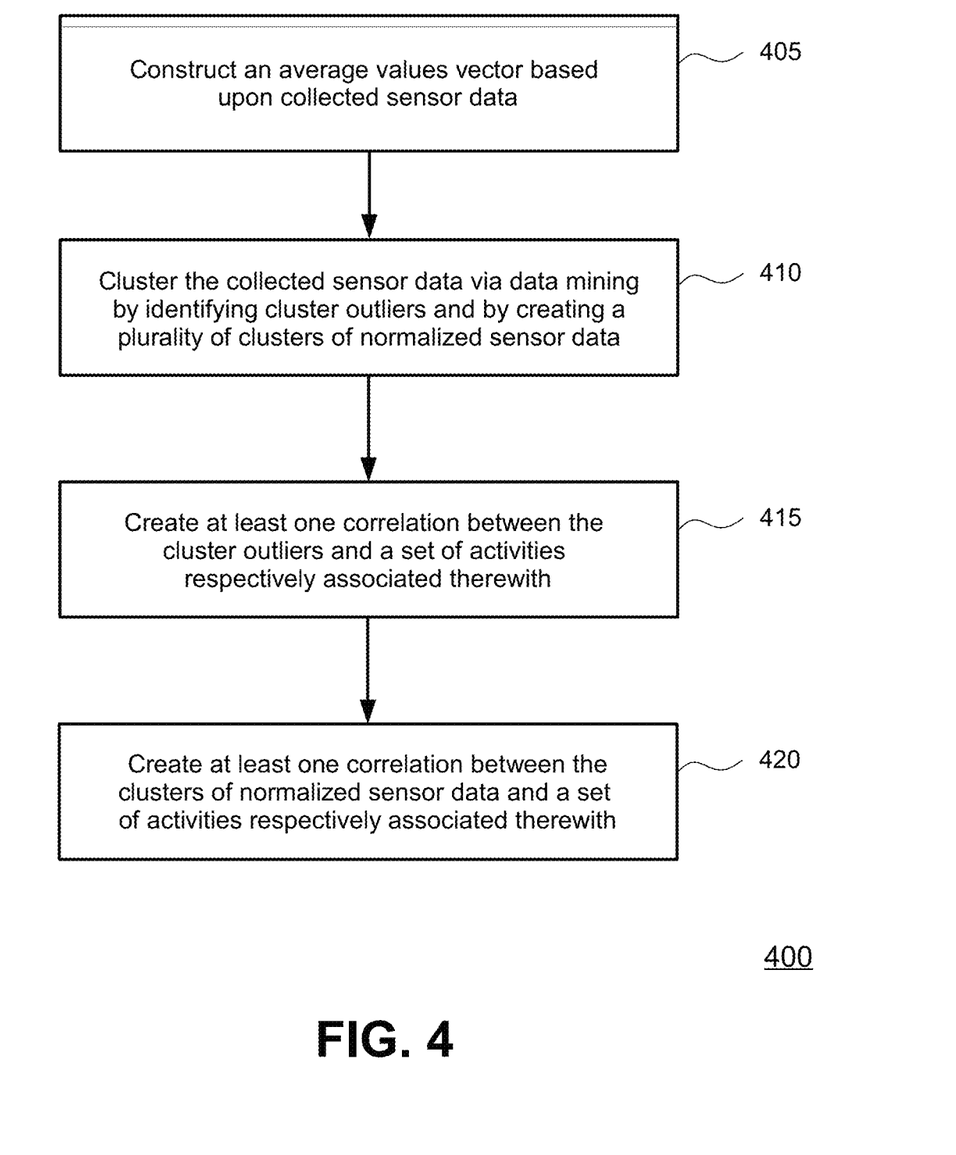
FIG. 4 illustrates a method of identifying one or more patterns in collected sensor data, according to an embodiment.

FIG. 4 illustrates a method 400 of identifying one or more patterns in collected sensor data, according to an embodiment. The method 400 provides an example embodiment with respect to step 310 of the method 300. In an embodiment, one or more steps of the method 400 may be facilitated via the feature extractor component of the analytical engine. The method 400 may begin at step 405, where the server application may construct an average values vector based upon the collected sensor data. An embodiment with regard to constructing the average values vector based upon the collected sensor data according to step 405 is described with respect to FIG. 5. At step 410, the server application may cluster the collected sensor data (i.e., may divide the collected sensor data into a number of clusters) via data mining. In an embodiment, the server application may divide the collected sensor data into clusters via a semi-supervised clustering method. For instance, the server application may divide the collected sensor data into "k" clusters through application of a k-means clustering algorithm. The server application may cluster the sensor data according to step 410 by identifying cluster outliers beyond one or more predetermined thresholds and distinguishing the cluster outliers from normalized sensor data within the one or more predetermined thresholds. Specifically, the server application may identify cluster outliers by calculating respective distances from the average values vector and comparing the respective distances against the one or more predetermined thresholds. The server application may identify sensor data points beyond the one or more predetermined thresholds as cluster outliers. As for the sensor data points within the one or more predetermined thresholds, the server application may create a plurality of clusters of normalized sensor data relevant to each of the plurality of chronological age groups defined for the age indices model. Accordingly, the server application may create normalized sensor data clusters that exclude the cluster outliers. In the context of the various embodiments described herein, optionally the server application may scale or may facilitate scaling of the normalized sensor data such that the server application may compare and analyze various data points of disparate magnitude.

At step 415, the server application may create at least one correlation between the cluster outliers and a set of activities respectively associated with the cluster outliers. The at least one correlation created at step 415 may reflect respective relationships between one or more of the cluster outliers and one or more of the associated set of activities. At step 420, the server application may create at least one correlation between the clusters of normalized sensor data and a set of activities respectively associated with the clusters of normalized sensor data. The at least one correlation created at step 420 may reflect respective relationships between one or more of the clusters of normalized sensor data and one or more of the associated set of activities. By creating correlations at steps 415 and 420, the server application may identify relevant data relationships to facilitate training of the age indices model at step 315 of the method 300. Specifically, the server application may focus upon activities associated with the normalized sensor data clusters while deemphasizing activities associated with the cluster outliers.

For instance, in the context of activity sensor data, at steps 405 and 410 the server application may cluster the activity data received in order to identify one or more patterns in various activities. Such clustering may include identifying cluster outliers and creating a plurality of clusters of normalized sensor activity data relevant to each of the plurality of chronological age groups. At steps 415 and 420, the server application may correlate the cluster outliers and a set of activities associated with the cluster outliers and additionally may correlate the respective clusters of normalized sensor data relevant to each chronological age group and a set of activities associated with the respective clusters. In an embodiment, the server application may correlate the various activities with health records among the individuals in each of the plurality of chronological age groups to determine whether limitation(s) in performance of one or more of the various activities are solely or partially consequent to one or more medical conditions.

Figure 5:
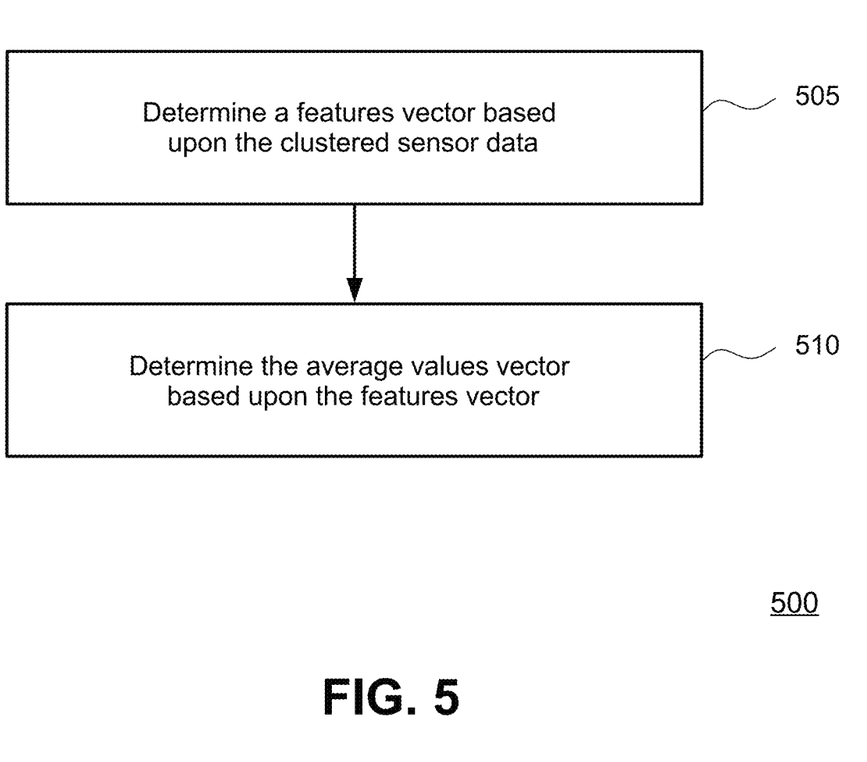
FIG. 5 illustrates a method of constructing an average values vector, according to an embodiment.

FIG. 5 illustrates a method 500 of constructing the average values vector based upon the collected sensor data, according to an embodiment. The method 500 provides an example embodiment with respect to step 405 of the method 400. In an embodiment, one or more steps of the method 500 may be facilitated via the feature extractor component of the analytical engine. The method 500 may begin at step 505, where the server application may determine a features vector based upon the clustered sensor data. Each feature of the features vector may represent a sensor measurement by one or more of the sensor devices in a particular context. The feature extractor component of the analytical engine may identify some or all of the features to be included in the features vector by analyzing aspects of unstructured sensor data collected by the sensor devices. At step 510, the server application may determine the average values vector based upon the features vector. The server application may determine the respective values of the average values vector by calculating an average among the data points provided for each respective feature of the feature vector.

As an example scenario in accordance with the various embodiments described herein, Subject Individual A may be a male having a chronological age of sixty. According to step 215 of the method 200, the server application may apply the age indices model to profile data associated with Subject Individual A. Assuming that activity data associated with Subject Individual A indicates that Subject Individual A is physically inactive, the server application may determine through application of the age indices model that Subject Individual A has a physiological age index of seventy. According to step 220, the server application may transmit the physiological age index for Subject Individual A to a Medical Professional A. Medical Professional A, taking into account that regular exercise may substantially improve key biological functions such as aerobic capacity, muscle strength, and immune functioning, may create a prescribed recommendation for Subject Individual A that includes a robust exercise routine having certain characteristics to target the effects of physical inactivity. The prescribed recommendation may include precise details with respect to type and/or frequency of suggested exercise in an attempt to lower the physiological age index of Subject Individual A such that it may more closely correspond to his chronological age. According to step 225, the server application may receive the prescribed recommendation for Subject Individual A and may process the recommendation by presenting the recommendation to Subject Individual A. According to steps 230 and 235, the server application may receive feedback with respect to the prescribed recommendation and may update the age indices model based upon the feedback. Such feedback may be implicit in the form of sensor data collected on Subject Individual A to determine whether Subject Individual A is in compliance with or has complied with the recommendation of Medical Professional A. Additionally or alternatively, such feedback may be explicit, e.g., in the form of written input from Subject Individual A. Furthermore, based upon an updated application of the age indices model consequent to receiving the feedback, the server application may determine whether the physiological age index of Subject Individual A has changed following the recommendation.

As a further example scenario in accordance with the various embodiments described herein, Subject Individual B may be a female having a chronological age of forty-five. According to step 215 of the method 200, the server application may apply the age indices model to profile data associated with Subject Individual B. Assuming that biosensor data associated with Subject Individual B indicates poor renal function, the server application may determine through application of the age indices model that Subject Individual B has a physiological age index of fifty-five. According to step 220, the server application may transmit the physiological age index for Subject Individual B to a Medical Professional B. Medical Professional B, taking into account the importance of physiological age in determining an appropriate dosage of prescription medication to improve renal function, may create a prescribed recommendation for Subject Individual B that includes a dosage of renal medication appropriate for an individual with a physiological age index of fifty-five, even though Subject Individual B is forty-five chronologically. According to step 225, the server application may receive the prescribed recommendation for Subject Individual B and may process the recommendation by presenting the recommendation to Subject Individual B. According to steps 230 and 235, the server application may receive feedback with respect to the prescribed recommendation and may update the age indices model based upon the feedback. Such feedback may be implicit in the form of sensor data collected on Subject Individual B to determine whether Subject Individual B is properly responding to the dosage of renal medication. Additionally or alternatively, such feedback may be explicit, e.g., in the form of written input from Subject Individual B or from a pharmacist describing the physical effects of the medication upon Subject Individual B. Furthermore, based upon an updated application of the age indices model consequent to receiving the feedback, the server application may determine whether the physiological age index of Subject Individual B has changed as a result of the prescribed dosage of renal medication and/or whether the prescribed dosage is appropriate.

As a further example scenario in accordance with the various embodiments described herein, Subject Individual C may be a female having a chronological age of seventy. According to step 215 of the method 200, the server application may apply the age indices model to profile data associated with Subject Individual C. Assuming that cognitive data associated with Subject Individual C indicates a pattern of poor memory and confusion, which the server application may determine via profile data metrics including statements made by Subject Individual C that reflect chronic failure to recall common life details, the server application may determine through application of the age indices model that Subject Individual C has a psychological age index of eighty. According to step 220, the server application may transmit the physiological age index for Subject Individual C to a Medical Professional C. Medical Professional C may create a prescribed recommendation for Subject Individual C by suggesting that Subject Individual C complete specified memory exercises and/or social activities, which may improve cognitive functioning per the age indices model. According to step 225, the server application may receive the prescribed recommendation for Subject Individual C and may process the recommendation by presenting the recommendation to Subject Individual C. According to steps 230 and 235, the server application may receive feedback with respect to the prescribed recommendation and may update the age indices model based upon the feedback. Such feedback may be implicit in the form of sensor data collected on Subject Individual C to determine whether Subject Individual C is properly responding to the specified memory exercises and/or social activities. Additionally or alternatively, such feedback may be explicit, e.g., in the form of informal or formal conversations between Subject Individual C and chatbot(s), Medical Professional C, and/or medical assistant(s). Furthermore, based upon an updated application of the age indices model consequent to receiving the feedback, the server application may determine whether the psychological age index of Subject Individual C has changed as a result of the specified memory exercises and/or social activities, e.g., by measuring the cognitive performance of Subject Individual C post-recommendation compared to her cognitive performance pre-recommendation.

As a further example scenario in accordance with the various embodiments described herein, Subject Individual D may be a male having a chronological age of twenty. According to step 215 of the method 200, the server application may apply the age indices model to profile data associated with Subject Individual D. Assuming that social data associated with Subject Individual D indicates a pattern of isolation, which the server application may determine via profile data points including statements made by Subject Individual D indicating anxiety and evidence indicating negative or minimal response to social networking activities initiated by Subject Individual D, the server application may determine through application of the age indices model that Subject Individual D has a social age index of fifteen. According to step 220, the server application may transmit the social age index for Subject Individual D to a Medical Professional D (e.g., a therapist). Medical Professional D may create a prescribed recommendation for Subject Individual D by suggesting that Subject Individual D initiate social interaction with friends/family and/or participate in one or more hobbies, which may reduce social isolation per the age indices model. According to step 225, the server application may receive the prescribed recommendation for Subject Individual D and may process the recommendation by presenting the recommendation to Subject Individual D. According to steps 230 and 235, the server application may receive feedback with respect to the prescribed recommendation and may update the age indices model based upon the feedback. Such feedback may be implicit in the form of sensor data collected on Subject Individual D to determine whether Subject Individual D is properly responding to the suggested social interaction and/or hobbies. Additionally or alternatively, such feedback may be explicit, e.g., in the form of informal or formal conversations between Subject Individual D and chatbot(s), Medical Professional D, and/or medical assistant(s). Furthermore, based upon an updated application of the age indices model consequent to receiving the feedback, the server application may determine whether the social age index of Subject Individual D has changed as a result of the prescribed social recommendations, e.g., by evaluating the social isolation of Subject Individual D post-recommendation in comparison to his social isolation pre-recommendation.

The descriptions of the various embodiments of the present invention have been presented for purposes of illustration but are not intended to be exhaustive or limited to the embodiments disclosed. All kinds of modifications made to the described embodiments and equivalent arrangements should fall within the protected scope of the invention. Hence, the scope of the invention should be explained most widely according to the claims that follow in connection with the detailed description, and should cover all possibly equivalent variations and equivalent arrangements. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A method comprising:
   receiving sensor data collected on a plurality of individuals via a plurality of sensor devices embedded in one or more artifacts associated with the plurality of individuals;
   constructing an age indices model by applying machine learning to the collected sensor data, wherein the age indices model includes stored or recorded correlations between normalized sensor data relevant to each of a plurality of chronological age groups and one or more of a plurality of functional age indices, and wherein the normalized sensor data is determined by dividing the collected sensor data via semi-supervised clustering; and
   determining one or more functional age indices among the plurality of functional age indices for a subject individual by applying the age indices model to profile data associated with the subject individual, wherein the one or more functional age indices include a psychological age index reflective of mental or cognitive health and a social age index reflective of behavioral expectations, interpersonal interaction, or cultural interaction.

2. The method of claim 1, further comprising:
   transmitting the one or more functional age indices determined for the subject individual to a professional or a knowledge base; and
   receiving and processing one or more prescribed recommendations for the subject individual, wherein the one or more prescribed recommendations include one or more treatments or lifestyle modifications.

3. The method of claim 2, further comprising:
receiving feedback with respect to the one or more prescribed recommendations, wherein the feedback includes sensor data collected on the subject individual; and
updating the age indices model based upon the feedback.

4. The method of claim 1, wherein the collected sensor data comprises at least one data type selected from the group consisting of activity data, biosensor data, cognitive data, and emotional data.

5. The method of claim 1, wherein constructing the age indices model comprises:
defining features of the age indices model, including the plurality of chronological age groups;
identifying one or more patterns in the collected sensor data to determine the normalized sensor data relevant to each of the plurality of chronological age groups;
applying a supervised learning algorithm to the normalized sensor data to train the age indices model, wherein training the age indices model comprises mapping the features of the age indices model to the normalized sensor data; and
responsive to training the age indices model, defining the plurality of functional age indices.

6. The method of claim 5, wherein training the age indices model further comprises:
selecting a group of individuals within one of the plurality of chronological age groups having a specified medical condition; and
training the age indices model based upon the specified medical condition.

7. The method of claim 5, wherein identifying the one or more patterns in the collected sensor data comprises:
constructing an average values vector based upon the collected sensor data;
clustering the collected sensor data via data mining, wherein clustering the collected sensor data comprises:
identifying cluster outliers by calculating respective distances from the average values vector and comparing the respective distances against one or more predetermined thresholds, and
creating a plurality of clusters of normalized sensor data relevant to each of the plurality of chronological age groups, wherein the clusters of normalized sensor data exclude the cluster outliers;
creating at least one correlation between the cluster outliers and a set of activities respectively associated with the cluster outliers; and
creating at least one correlation between the clusters of normalized sensor data and a set of activities respectively associated with the clusters of normalized sensor data.

8. The method of claim 7, wherein constructing the average values vector comprises:
determining a features vector based upon the clustered sensor data, wherein each feature of the features vector represents a particular sensor measurement in a particular context; and
determining the average values vector based upon the features vector.

9. The method of claim 5, wherein the supervised learning algorithm is a multiclass classification algorithm.

10. The method of claim 1, wherein the one or more functional age indices further include a physiological age index reflective of physical health.

11. A computer program product comprising a computer readable storage medium having program instructions embodied therewith, the program instructions executable by a computing device to cause the computing device to:
receive sensor data collected on a plurality of individuals via a plurality of sensor devices embedded in one or more artifacts associated with the plurality of individuals;
construct an age indices model by applying machine learning to the collected sensor data, wherein the age indices model includes stored or recorded correlations between normalized sensor data relevant to each of a plurality of chronological age groups and one or more of a plurality of functional age indices, and wherein the normalized sensor data is determined by dividing the collected sensor data via semi-supervised clustering; and
determine one or more functional age indices among the plurality of functional age indices for a subject individual by applying the age indices model to profile data associated with the subject individual, wherein the one or more functional age indices include a psychological age index reflective of mental or cognitive health and a social age index reflective of behavioral expectations, interpersonal interaction, or cultural interaction.

12. The computer program product of claim 11, wherein the program instructions further cause the computing device to:
transmit the one or more functional age indices determined for the subject individual to a professional or a knowledge base; and
receive and process one or more prescribed recommendations for the subject individual, wherein the one or more prescribed recommendations include one or more treatments or lifestyle modifications.

13. The computer program product of claim 12, wherein the program instructions further cause the computing device to:
receive feedback with respect to the one or more prescribed recommendations, wherein the feedback includes sensor data collected on the subject individual; and
update the age indices model based upon the feedback.

14. The computer program product of claim 11, wherein constructing the age indices model comprises:
defining features of the age indices model, including the plurality of chronological age groups;
identifying one or more patterns in the collected sensor data to determine the normalized sensor data relevant to each of the plurality of chronological age groups;
applying a supervised learning algorithm to the normalized sensor data to train the age indices model, wherein training the age indices model comprises mapping the features of the age indices model to the normalized sensor data; and
responsive to training the age indices model, defining the plurality of functional age indices.

15. The computer program product of claim 14, wherein training the age indices model further comprises:
selecting a group of individuals within one of the plurality of chronological age groups having a specified medical condition; and
training the age indices model based upon the specified medical condition.

16. A system comprising:
a processor; and
a memory storing an application program, which, when executed on the processor, performs an operation comprising:

receiving sensor data collected on a plurality of individuals via a plurality of sensor devices embedded in one or more artifacts associated with the plurality of individuals;

constructing an age indices model by applying machine learning to the collected sensor data, wherein the age indices model includes stored or recorded correlations between normalized sensor data relevant to each of a plurality of chronological age groups and one or more of a plurality of functional age indices, and wherein the normalized sensor data is determined by dividing the collected sensor data via semi-supervised clustering; and determining one or more functional age indices among the plurality of functional age indices for a subject individual by applying the age indices model to profile data associated with the subject individual, wherein the one or more functional age indices include a psychological age index reflective of mental or cognitive health and a social age index reflective of behavioral expectations, interpersonal interaction, or cultural interaction.

17. The system of claim 16, wherein the operation further comprises:

transmitting the one or more functional age indices determined for the subject individual to a professional or a knowledge base; and receiving and processing one or more prescribed recommendations for the subject individual, wherein the one or more prescribed recommendations include one or more treatments or lifestyle modifications.

18. The system of claim 17, wherein the operation further comprises:

receiving feedback with respect to the one or more prescribed recommendations, wherein the feedback includes sensor data collected on the subject individual; and updating the age indices model based upon the feedback.

19. The system of claim 16, wherein constructing the age indices model comprises:

defining features of the age indices model, including the plurality of chronological age groups;

identifying one or more patterns in the collected sensor data to determine the normalized sensor data relevant to each of the plurality of chronological age groups;

applying a supervised learning algorithm to the normalized sensor data to train the age indices model, wherein training the age indices model comprises mapping the features of the age indices model to the normalized sensor data; and responsive to training the age indices model, defining the plurality of functional age indices.

20. The system of claim 19, wherein training the age indices model further comprises:

selecting a group of individuals within one of the plurality of chronological age groups having a specified medical condition; and training the age indices model based upon the specified medical condition.

* * * * *